United States Patent
Ward et al.

(10) Patent No.: US 9,476,823 B2
(45) Date of Patent: Oct. 25, 2016

(54) BORESCOPE STEERING ADJUSTMENT SYSTEM AND METHOD

(71) Applicant: General Electric Company, Schenectady, NY (US)

(72) Inventors: Thomas Charles Ward, Auburn, NY (US); Bryan David Maule, Camillus, NY (US); Melissa Rose Stancato, Syracuse, NY (US); Matthew William Pankow, Camillus, NY (US); David Scott Andreasen, Boston, MA (US)

(73) Assignee: General Electric Company, Schenectady, NY (US)

(*) Notice: Subject to any disclaimer, the term of this patent is extended or adjusted under 35 U.S.C. 154(b) by 322 days.

(21) Appl. No.: 13/949,010

(22) Filed: Jul. 23, 2013

(65) Prior Publication Data

US 2015/0029500 A1  Jan. 29, 2015

(51) Int. Cl.
*H04N 9/47* (2006.01)
*A62B 1/04* (2006.01)
*G01N 21/01* (2006.01)
(Continued)

(52) U.S. Cl.
CPC ............. *G01N 21/01* (2013.01); *B25J 9/1635* (2013.01); *E21B 47/0002* (2013.01); *G02B 23/24* (2013.01); *G01N 2021/0112* (2013.01); *G01N 2021/0181* (2013.01); *G05B 2219/23092* (2013.01); *G05B 2219/35478* (2013.01); *G05B 2219/37396* (2013.01); *G05B 2219/39443* (2013.01); *G05B 2219/45066* (2013.01); *G06F 3/0482* (2013.01); *G06F 3/0488* (2013.01); *G06F 3/04847* (2013.01)

(58) Field of Classification Search
USPC ...................... 348/61, 63, 64, 65, 74, 77, 82
See application file for complete search history.

(56) References Cited

U.S. PATENT DOCUMENTS

| 7,148,923 B2 | 12/2006 | Harper |
| 7,268,924 B2 | 9/2007 | Hussey |

(Continued)

FOREIGN PATENT DOCUMENTS

| EP | 1787572 A1 | 5/2007 |
| FR | 2965369 A1 | 3/2012 |

OTHER PUBLICATIONS

High Defineition VideoScope, User Guide, Extech Instruments a Flir Company, Oct. 12, 2012.*

(Continued)

*Primary Examiner* — Daquan Zhao
(74) *Attorney, Agent, or Firm* — Fletcher Yoder, P.C.

(57) ABSTRACT

Systems and methods provided herein. In one embodiment, a borescope system includes a probe to capture images and a display a settings menu, measurements, the images captured by the probe, or any combination thereof. In addition, the borescope system a processor programmed to display a user interface to enable a user to control movement of the probe, adjust settings, navigate menus, make selections, or any combination thereof. The processor is communicatively coupled to the probe, and the display, and is programmed to instruct the borescope to enter a live menu view when an articulation mode is selected from the settings menu. In the live menu view, the processor is programmed to instruct the display to display the images captured by the probe, and to enable a user to control the movement of the probe and adjust articulation sensitivity of the probe while viewing the images on the display.

20 Claims, 5 Drawing Sheets (51) Int. Cl.
*E21B 47/00* (2012.01)
*B25J 9/16* (2006.01)
*G02B 23/24* (2006.01)
*A61B 1/04* (2006.01)
*A61B 1/06* (2006.01)
*G06F 3/0482* (2013.01)
*G06F 3/0484* (2013.01)
*G06F 3/0488* (2013.01)

(56) References Cited

U.S. PATENT DOCUMENTS

| | | |
|---|---|---|
| 7,878,406 B2 | 2/2011 | Pankow |
| 7,967,205 B2 | 6/2011 | Pankow |
| 8,387,881 B2 | 3/2013 | Volkinburg |
| 8,439,264 B2 | 5/2013 | Barber |
| 2002/0125323 A1 | 9/2002 | Marrs, Jr. |
| 2007/0226258 A1* | 9/2007 | Lambdin et al. .......... 707/104.1 |
| 2009/0131753 A1 | 5/2009 | Amano et al. |
| 2012/0193429 A1 | 8/2012 | Volkinburg |
| 2013/0048734 A1 | 2/2013 | Bianconi |
| 2013/0139112 A1 | 5/2013 | Domke |
| 2014/0139658 A1* | 5/2014 | Dhanvantri et al. ............ 348/85 |

OTHER PUBLICATIONS

PCT Search Report and Written Opinion issued in connection with corresponding Application No. PCT/US2014044085 on Oct. 7, 2014.

* cited by examiner

BORESCOPE STEERING ADJUSTMENT SYSTEM AND METHOD

BACKGROUND OF THE INVENTION

The present disclosure relates generally to the inspection of equipment and facilities, and more particularly to borescope systems used for the inspection.

Certain equipment and facilities, such as power generation equipment and facilities, oil and gas equipment and facilities, aircraft equipment and facilities, manufacturing equipment and facilities, and the like, include a plurality of interrelated systems, and processes. For example, power generation plants may include turbine systems and processes for operating and maintaining the turbine systems. Likewise, oil and gas operations may include carbonaceous fuel retrieval systems and processing equipment interconnected via pipelines. Similarly, aircraft systems may include airplanes and maintenance hangars useful in maintaining airworthiness and providing for maintenance support.

Certain techniques, such as non-destructive inspection techniques or non-destructive testing (NDT) techniques, may be used to inspect and facilitate maintenance of such equipment and facilities. For example, a borescope system may be utilized in an NDT technique to inspect the internals without disassembly of a wide variety of equipment and facilities. Specifically, a borescope probe may be inserted into various openings of the equipment or facility to provide illumination and/or visual observations of the internals of the equipment or facility. Accordingly, it would be beneficial to improve the configuration of such borescope systems, for example, to enable a user to more accurately and efficiently adjust settings as desired.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a borescope system includes a probe to capture images and a display a settings menu, measurements, the images captured by the probe, or any combination thereof. In addition, the borescope system includes a processor programmed to display a user interface to enable a user to control movement of the probe, adjust settings, navigate menus, make selections, or any combination thereof. The processor is communicatively coupled to the probe, and the display, and is programmed to instruct the borescope to enter a live menu view when an articulation mode is selected from the settings menu. In the live menu view, the processor is programmed to instruct the display to display the images captured by the probe, and to enable a user to control the movement of the probe and adjust articulation sensitivity of the probe while viewing the images on the display.

In a second embodiment, a tangible non-transitory computer readable medium storing instructions executable by a processor of a borescope system includes instructions to enter a settings menu displayed by a display included in the borescope system that further includes a probe, to select an articulation mode of the probe from the settings menu, to automatically enter a live menu view in response to selection of the articulation mode, and in the live menu view, to enable a user to control the probe and adjust the articulation sensitivity of the probe.

In a third embodiment, a method includes entering a settings menu, selecting an articulation mode of the borescope system probe from the settings menu, automatically entering a live menu view, and in the live menu view, enabling a user to control the borescope system probe and adjust the articulation sensitivity of the borescope system probe.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure may apply to a variety of inspection techniques and systems, including non-destructive testing (NDT) techniques/systems. In some embodiments of an NDT system, a borescope system may be utilized to facilitate testing and/or inspection of equipment and facilities, such as power generation equipment and facilities, oil and gas equipment and facilities, and aircraft equipment and facilities, by providing illumination, visualization, and/or other data relating to the internals of the equipment or facilities.

A borescope generally includes a user controllable probe with a camera and an illumination device. More specifically, a user may control the movement (e.g., articulation) of the probe to illuminate or visually capture a desired location within the equipment or facility. In other embodiments, the borescope may include various other user controllable probes (i.e., tips) to facilitate x-ray inspection, eddy current inspection, and/or ultrasonic inspection. To enhance the user's control of the movement of the probe, the borescope may include field-adjustable settings, such as articulation sensitivity and articulation mode, which enable user configuration of the movement of the probe as desired. As used herein, "field-adjustable settings" describe settings that may be adjusted during operation of the borescope system 14 including remotely over a network (e.g., a wide area network or a local area network). Accordingly, by providing for field-adjustable settings, such as the articulation sensitivity and the articulation mode, the borescope system may provide a more efficient and detailed inspection of a desired machinery or process.

Accordingly, one embodiment of the present disclosure describes a borescope system including a probe that captures images, and a display that displays a settings menu, measurements, the images captured by the probe, or any combination thereof. In addition, the borescope system includes a processor programmed to display a user interface to enable a user to control movement of the probe, adjust settings, navigate menus, make selections, or any combination thereof. The processor is communicatively coupled to the probe, and the display, and is programmed to instruct the borescope to enter a live menu view when an articulation mode is selected from the settings menu. In the live menu view, the processor is programmed to instruct the display to display the images captured by the probe, and to enable a user to control the movement of the probe and adjust articulation sensitivity of the probe while viewing the images on the display. As will be appreciated by persons of ordinary skill in the relevant art, the techniques described in the present disclosure may be utilized in other NDT systems 10, such as an endoscope system.

Figure 1:
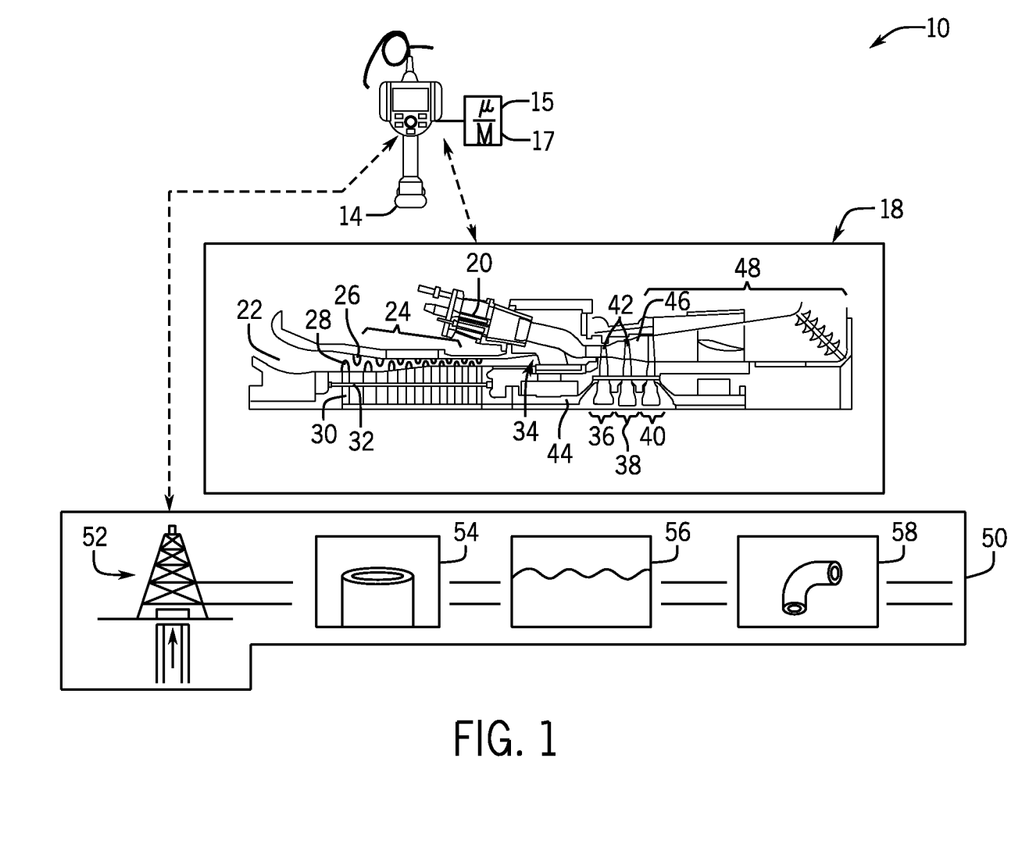
FIG. 1 is a block diagram illustrating an embodiment of a non-destructive testing (NDT) system, including a borescope system, in accordance with an embodiment.

By way of introduction, FIG. 1 depicts an embodiment of a non-destructive testing (NDT) system 10. As depicted, the NDT system 10 may include one or more NDT inspection devices, such as a borescope system 14. In some embodiments, the borescope 14 may be a XL GO+ VideoProbe, a XLG3 VideoProbe, XL Vu VideoProbe, or the like, available from General Electric Company, of Schenectady, N.Y. The depicted borescope 14 includes one or more processors 15 and memory 17 that may be used to facilitate the functionality of the borescope, such as visually inspecting equipment and facilities. As used herein, a "processor" refers to any number of processor components related to the borescope system 14. For example, in some embodiments, the processor 15 may be coupled to and programmed to instruct components of the borescope system 14 such as the probe, the display, and the user interface (e.g., buttons and joystick). Furthermore, in some embodiments, the processor 15 may be located locally or remotely, for example, in the "cloud."

In operation, the borescope 14 may be inserted into a plurality of access ports and other locations of equipment such as turbomachinery 18 to provide for illumination and visual observations of a number of components of the turbomachinery 18, such as the nozzles 20, intake 22, compressor 24, vanes 26, blades 28, wheels 30, shaft 32, diffuser 34, stages 36, 38, and 40, blades 42, shaft 44, casing 46, and exhaust 48. Other types of equipment that the borescope 14 may inspect include compressors, pumps, turbo expanders, wind turbines, hydroturbines, industrial equipment, residential equipment, and the like. Additionally, the borescope 14 may be used to inspect the facilities, such as an oil and gas facility 50. For example, the borescope 14 may visually inspect oil and gas equipment 52 including the interior of pipes or conduits 54, underwater (or underfluid) locations 56, and difficult to observe locations such as locations having curves or bends 58. While inspecting the equipment and facilities, the borescope 14 may gather data including but not limited to images, video, and sensor measurements, such as temperature, pressure, flow, clearance (e.g., measurement between a stationary component and a rotary component), and distance measurements.

Figure 2:
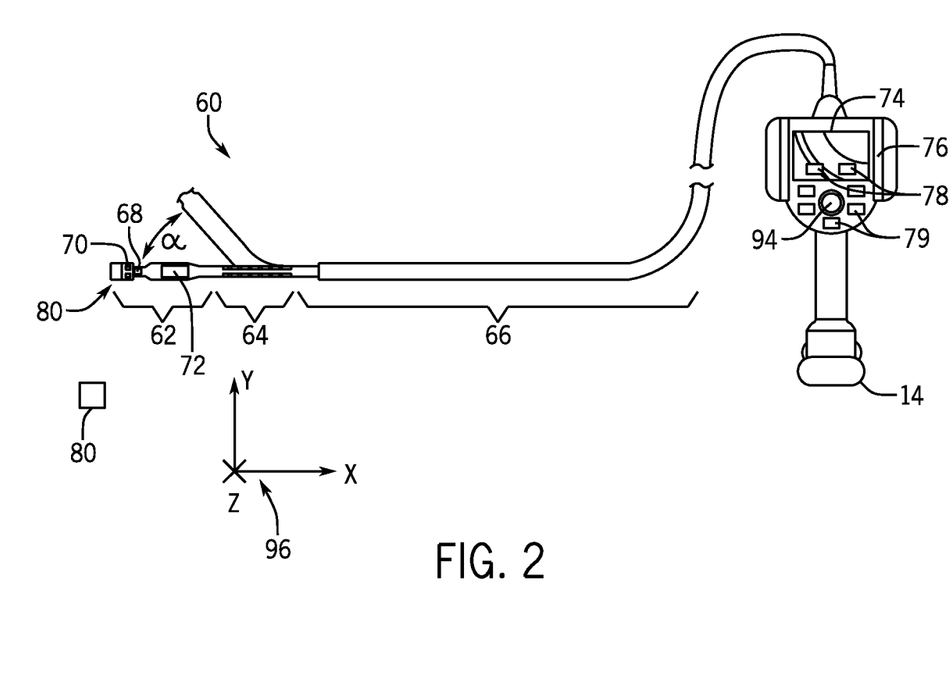
FIG. 2 is a front view of the borescope system of FIG. 1, in accordance with an embodiment.

The borescope 14 may includes various components such as the ones depicted in the schematic view of the borescope depicted in FIG. 2. The borescope system 14 includes an insertion tube 60 suitable for insertion into a variety of location, such as inside of the turbomachinery 18, equipment 52, pipes or conduits 54, underwater locations 56, curves or bends, and so on. The insertion tube 60 includes a probe section 62, an articulating section 64, and a conduit section 66. In the depicted embodiment, the probe 60 includes a camera 68, one or more lights 70 (e.g., LEDs), and sensors 72. The borescope's camera 68 provides images and video suitable for inspection and the lights 70 provide for illumination when the probe 62 is disposed in locations having low light or no light.

For example, the camera 68 may capture an image or video (e.g., a plurality of time-captured images) 74, which is then displayed on a screen 76 of the borescope 14. The screen 76 may display menus, measurements, images captured by the probe 62, or any combination thereof. In some embodiments, the borescope screen 76 is a multi-touch-screen that uses capacitance techniques, resistive techniques, infrared grid techniques, and the like. The borescope screen 76 includes soft buttons 78 that detect the touch (e.g., activation) of a stylus and/or one or more human fingers. Additionally, hard buttons 79 may be included on the borescope 14 to replace or supplement the soft buttons 78.

The borescope system 14 increases the information displayed by overlaying certain data onto the image 74. For example, a borescope tip map may be overlaid on the video to show an approximation of the disposition of the probe 62 during insertion so as to guide a user to more accurately position the borescope camera 68. A variety of other overlays may be provided including measurement overlays, menu overlays, annotation overlays, and object identification overlays. The image or video 74 may then be displayed with the overlays generally displayed on top of the image or video 74.

In addition to collecting visual data, the borescope 14 may collect other data, such as sensor 72 data. Accordingly, in certain embodiments, the borescope 14 may include a plurality of removable replacement probes 80 to facilitate capturing data such as temperature data, distance data, clearance data (e.g., distance between a rotating and a stationary component), flow data, and so on. For example, one replacement probe 80 may project a shadow onto the image captured by the probe to indicate distance. Another replacement probe 80 may utilize a prism to display both a right and a left view. Other examples of the replacement probes 80 include retrieval tips such as snares, magnetic tips, or gripper tips; and cleaning and obstruction removal tools, such as wire brushes, or wire cutters.

Figure 3:
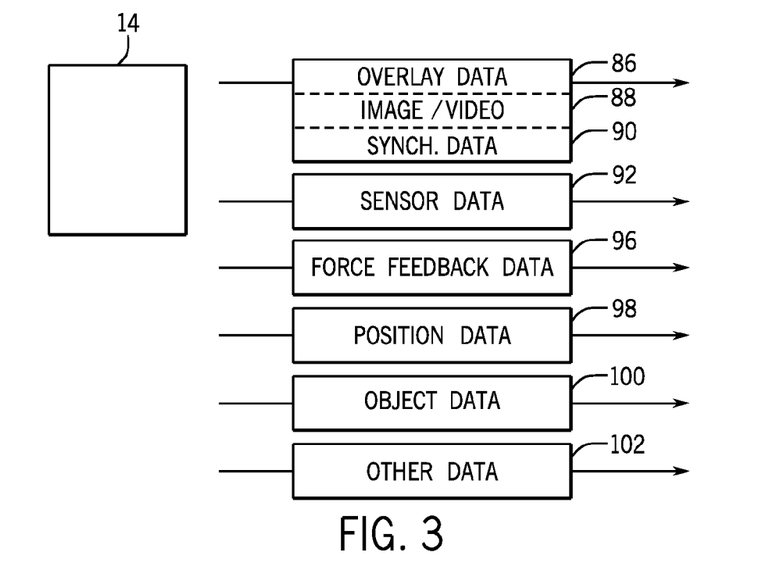
FIG. 3 is a block diagram illustrating data gathered by the borescope system of FIG. 1, in accordance with an embodiment.

One embodiment of the data collected by the borescope 14 is depicted in FIG. 3. As depicted, the image 74 and overlays is separated into two or more data streams 86 and 88. The data stream 86 may include only overlay data, while the data stream 88 may include images or video data. In one embodiment, the images or video data 88 may be synchronized with the overlay data 86 using a synchronization signal 90. Additionally the sensor data 92 gathered by the sensor 72 may also be synchronized with the overlay data 86. For example, this enables overlay tip maps to be displayed alongside with temperature information, pressure information, flow information, clearance, and so on. Likewise, sensor data 92 may be displayed alongside the image or video data 88.

Turning back to FIG. 2, a user controls the articulating section 64 with, for example, a physical joystick 94 to move the position of the probe 62. Accordingly, the articulation sections 64 steers or "bends" in various dimensions. For example, the articulation section 64 may enable movement of the probe 62 in an X-Y plane X-Z plane and/or Y-Z plane of the depicted XYZ axes 96. Accordingly, the physical joystick 94 may be used to provide control actions suitable for disposing the probe 62 in a variety of angles, such as the depicted angle a. Indeed, probe 62 may be disposed in any angle a with respect to the XYZ axes 96 to observe a desired location. In this manner, the borescope probe 62 may be positioned to visually inspect desired locations. Furthermore, in some embodiments, the physical joystick 94 may provide force feedback or haptic feedback to the user. For example, the joystick 94 may utilize haptic feedback to communicate that the probe 62 is abutting or contacting a structure, vibrations felt by the probe 62, force related to flows, temperatures, clearances, pressures, articulation sensitivity of the probe 62 and the like. Accordingly, as depicted in FIG. 3, the data collected by the borescope 14 includes force feedback data 96.

Additionally, the borescope system 14 collects position data 98, object data 100, and other types of data 102. For example, the position data 98 may include locations of the borescope 14 in relation to equipment 18, and/or facilities 50. Object data 100 may include data related to the object under inspection. For example, the object data 180 may include identifying information (e.g., serial numbers), observations on equipment condition, annotations (textual annotations, voice annotations), and so on. Other types of data 102 include menu-driven inspection data, which when used provides a set of pre-defined "tags" that can be applied as text annotations and metadata.

Figure 4:
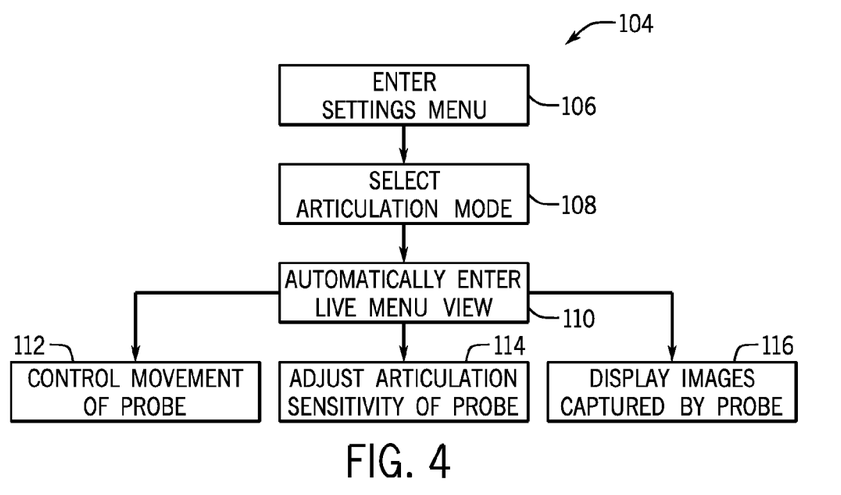
FIG. 4 is a flow diagram illustrating a process for adjusting the articulation settings of a borescope probe in the borescope system of FIG. 2, in accordance with an embodiment.

As described above, a user may utilize the physical joystick 94 to control the positioning of the probe 62. The borescope system 14 includes various settings, such as articulation mode and articulation sensitivity, to enable the user to better control the movement of the probe 62. One example of a process 104 for configuring the articulation settings (e.g., mode and sensitivity) of the probe 62 is depicted in FIG. 4. As depicted, the process 104 begins when a settings menu is entered (process block 106). In the settings menu, an articulation mode is selected (process block 108). The articulation mode describes "how" the probe 62 articulates. Once the articulation mode is selected, the borescope 14 automatically enters a live menu view (process block 110). In the live menu view, a user is able to control the movement of the probe via the articulation section (process block 112) and adjust the articulation sensitivity of the probe (process block 114) while viewing the images captured by the probe (process block 116). In other words, process 104 enables the user to adjust articulation settings and immediately experiment with the results. The articulation sensitivity describes the probe's reaction to user controls. Additionally or alternatively, the borescope 14 may enter the live menu view in response to other indications of the user's desire to adjust the articulation sensitivity of the probe 62. For example, this may include the user activating a dedicated articulation sensitivity button.

Figure 5:
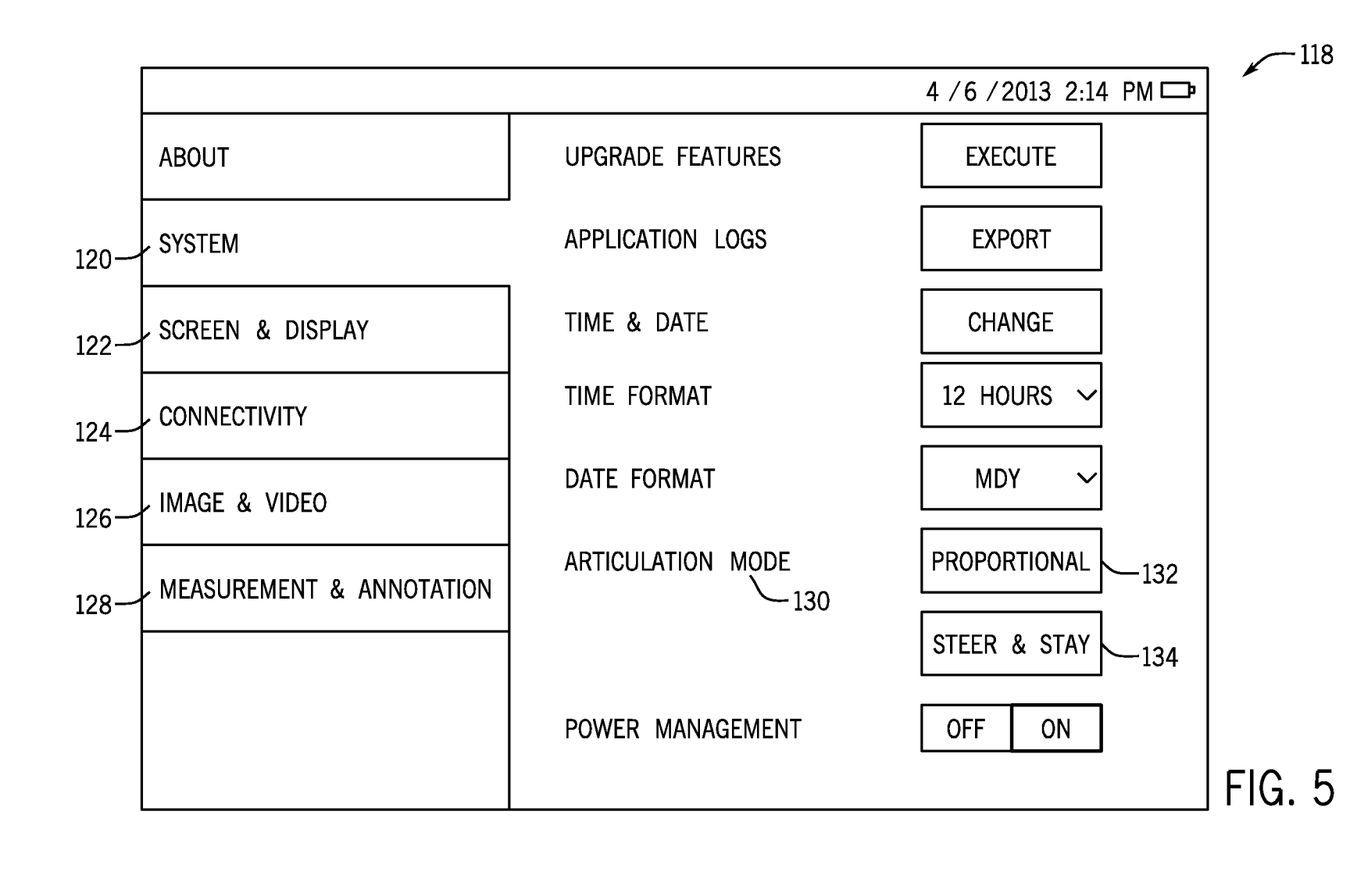
FIG. 5 is a screen view of a settings menu displayed on the borescope system of FIG. 2, in accordance with an embodiment.

More specifically, an embodiment of a settings menu 118 is depicted in FIG. 5. The settings menu 118 is displayed to a user on the borescope screen 76, which as described above may be a multi-touchscreen. The user may interact with the settings menu 118 by selecting various soft buttons with a finger or a stylus. The settings menu 118 may be broken down into smaller categories to assist the user in locating the desired setting. In the depicted embodiment, the settings menu 118 includes a System settings menu 120, a Screen & Display settings menu 122, a Connectivity settings menu 124, an Image & Video settings menu 126, and a Measurement & Annotation settings menu 128. The user may navigate between each of the menus (e.g., 118-126) by selecting (e.g., activating) the name of the desired menu from the settings menu 118.

Each menu includes various settings that enable a user to configure the borescope system 14. For example, the depicted System settings menu 120 enables the user to upgrade features, export application logs, set/format the time and date, choose an articulation mode, and turn on/off power management. The setting of particular interest in the present disclosure is the Articulation Mode setting 130, which configures "how" the probe 62 moves. As depicted, the Articulation Mode setting 130 includes a choice between a Proportional mode 132 and a Steer & Stay mode 134. In both the Proportional mode 132 and the Steer & Stay mode 134, the probe 62 is configured to move based on user input into the physical joystick 94. For example, when a user moves the joystick 94 right, the probe 62 also moves to the right and when the user moves the joystick 94, the probe 62 also moves up, and so on. However, in a Proportional mode 132, when the user releases the joystick 94 (i.e., stops controlling the movement of the probe 62), the probe 62 moves back to its neutral or central position. On the other hand, in a Steer & Stay mode, the probe 62 remains in its last position.

Figure 6:
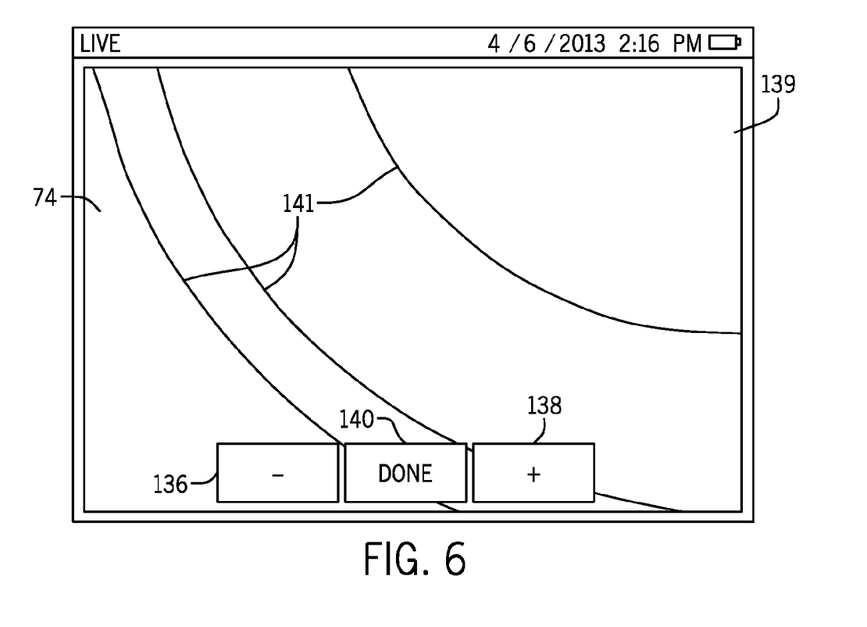
FIG. 6 is a screen view of a first embodiment of a live menu view displayed on the borescope system of FIG. 2, in accordance with an embodiment.
Figure 7:
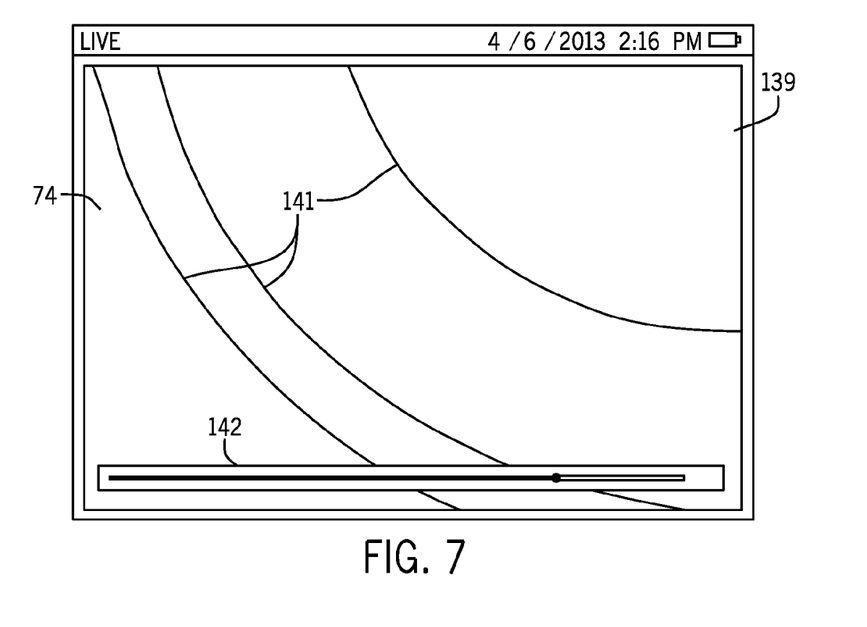
FIG. 7 is a screen view of a second embodiment of a live menu view displayed on the borescope system of FIG. 2, in accordance with an embodiment.

When one of the articulation modes (e.g., proportional mode or steer & stay mode) is selected, the borescope automatically enters a live menu view in response, which enables a user to adjust the articulation sensitivity of the probe 62. Embodiments of the live menu view are depicted in FIGS. 6 and 7. In both embodiments, a live view of the images 74 captured by the probe 62 is displayed on the borescope screen 76. In other words, as the probe 62 moves, the images 74 displayed on the screen 76 will change accordingly. In addition, while viewing the images 74, the user may increase and/or decrease the articulation sensitivity of the probe 62. More specifically, the user may increase the articulation sensitivity of the probe 62 so that the probe will be more responsive to movements of the joystick 94. On the other hand, the user may decrease the articulation sensitivity of the probe 62 so that the probe will be less responsive to movements of the joystick 94. In other words, as the articulation sensitivity increases the probe 62 moves more in relation to each joystick 94 movement and vice versa. In some embodiments, this may include utilizing a stepper motor in the articulation section 64. For example, when the articulation sensitivity is set at 50%, a 1 mm move of the joystick 94 may cause the stepper motor to move five steps in the direction the joystick 94 was moved, and when the articulation sensitivity is increase to 60%, a 1 mm move of the joystick 94 may cause the stepper motor to move six steps in the direction the joystick 94 was moved.

As described above, the haptic feedback may be provided based on the articulation sensitivity of probe 62. More specifically, the joystick 94 may be stiffer (e.g., more resistant to movement) when the sensitivity is lower to facilitate more precise movement of the probe 62, and looser (e.g., less resistant to movement) when the sensitivity is higher to enable quicker movement of the probe 62.

In the embodiments depicted in FIGS. 6 and 7, soft buttons displayed on the screen 76 are utilized to adjust the articulation sensitivity. For example, in FIG. 6, the screen 76 displays a decrease button (−) 136, an increase button (+) 138, and a Done button 140. The FIGS. 6 and 7 also depict an image 139 having features 141. The image 139 (e.g., static image or video image) corresponds to a component undergoing observation. The features 141 may correspond to, for example, ridges manufactured into the component. In the depicted embodiments, when the decrease button 136 is selected, the articulation sensitivity will decrease, and when the increase button 138 is selected, the articulation sensitivity increases. Accordingly, the articulation sensitivity may be adjusted so that the features 141 may be more easily observed. For example, by decreasing the articulation sensitivity, a movement of the joystick 94 may result in the image 139 shifting a smaller distance more suitable to observe the features 141 at higher magnification. Likewise, increasing the articulation sensitivity may provide for faster observations at lower magnifications with less movement of the joystick 94. In other words, the articulation sensitivity may be adjusted so that a certain joystick 94 movement (e.g., 0.5, 1, 2, 3, 4, 5, 6, 7, 10 mm or more) corresponds to a larger of smaller movement of the articulation section 64 (e.g., 0.05, 0.5, 1, 2, 3, 4, 5, 6, 7, 10 mm or more), and thus movement of the image.

Similarly, in FIG. 7, the screen 76 displays a slider 142. In the depicted embodiment, when the slider 142 is slid to the right, the articulation sensitivity increases, and when the slider is slid to the left, the articulation sensitivity decreases. For example, moving the slider 1, 2, 3, 5, 6, 7, 8% or more of the total slider length may result in increases or decreases of (e.g., 0.5, 1, 2, 3, 4, 5, 6, 7, 10 mm or more) of movement of the articulation section 64 with the same amount of movement of the joystick 94. As should be appreciated, hard buttons 79 on the borescope 14 may also be utilized to supplement or replace the soft buttons (e.g., 136, 138, 140, and 142). By overlaying the slider 142 (and buttons 136, 138, 140) on the image 139, adjustments to the articulation sensitivity may be performed during inspection, and the results of the adjustments may then be observed. It is to be noted that other controls may be used in addition to or in lieu of the slider 142 and buttons 136, 138, 140. For example, a textbox may be used to enter a desired articulation sensitivity as a numeric value or as a percentage. Likewise, a touch-control dial, selectable preset settings (e.g., "high", "medium," and "low"), radio buttons, dropdown menus having various articulation sensitivity values, and so on, may be used. It is also to be noted that, in another embodiment, the slider 142 may be displayed vertically or at an angle.

As described above, as the articulation sensitivity is adjusted, the user can experiment with the adjusted settings to determine whether further adjustment is desired. For example, a user may select the increase button 138 to increase the articulation sensitivity. After the articulation sensitivity is increased, the user may test the movement of the probe 62 with the increased sensitivity. The user may then decide whether to adjust the articulation sensitivity further. Once the user is satisfied with the articulation sensitivity, in some embodiments, the user may select the Done button 140 and return to the settings menu 118. In other embodiments, the user may simply continue using the borescope 14 with the articulation sensitivity controls (e.g., 136, 138 and 142) on the screen. In other words, the articulation sensitivity may continue to be adjustable during normal operation of the borescope 14. For example, this may enable the user to better navigate tight areas by decreasing articulation sensitivity and to increase articulation sensitivity to expedite the movement of the probe 14.

Technical effects of the invention include providing systems and methods that improve the configuration of a borescope 14. More specifically, adjustments to the settings of the borescope 14 may be tested in a live menu view. For example, in the live menu view, when the articulation sensitivity of the borescope 14 is increased/decreased, the movement of the probe 62 may be tested to determine whether further adjustment is desired. In other words, embodiments of the present disclosure improve the efficiency and accuracy of configuring the settings of the borescope 14 by enabling the settings to be adjusted in a live view.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A borescope system comprising:
a probe configured to capture images;
input devices configured to receive user inputs to the borescope system, wherein the input devices comprises a physical joystick, a hard button, one or more soft controls, or any combination thereof; and
a display configured to:
display a settings menu configured to enable the user inputs to select an articulation mode setting of the probe from the settings menu; and
display a live menu view when the articulation mode is selected, wherein the live menu view comprises:
a first image captured by the probe; and
a second image of a first soft control overlaid on the first image to enable the user inputs to adjust an articulation sensitivity setting of the probe via the first soft control and to control articulation of the probe based at least in part on the articulation sensitivity setting while the images captured by the probe are displayed, wherein the articulation sensitivity setting indicates an amount the probe moves in response to the user inputs that control articulation of the probe.

2. The borescope system of claim 1, wherein, in the live menu view, the first soft control is configured to enable the user inputs to increase, decrease, or a combination thereof, the articulation sensitivity setting of the probe.

3. The borescope system of claim 2, wherein the live menu view comprises a third image of a second soft control overlaid on the first image;
wherein the borescope system is configured to increase the articulation sensitivity setting when the user inputs select the second soft control and to decrease the articulation sensitivity setting when the user inputs select the first soft control.

4. The borescope system of claim 2, wherein the first soft control comprises a slider displayed horizontally across the display, wherein the borescope system is configured to increase the articulation sensitivity setting when the user inputs comprise a first slide of the slider right and to decrease the articulation sensitivity setting when the user inputs comprise a second slide of the slider left.

5. The borescope system of claim 1, wherein the probe is configured to return to center when the user inputs are not controlling the articulation of the probe and the user inputs select a proportional mode as the articulation mode setting.

6. The borescope system of claim 1, wherein the probe is configured to remain in a last articulated position when the user inputs are not controlling the articulation of the probe and the user inputs select a steer & stay mode as the articulation mode setting.

7. The borescope of system claim 1, wherein the input devices comprise a haptic device configured to provide haptic feedback to a user of the borescope system based at least in part on the articulation of the probe, the articulation sensitivity setting of the probe, or both.

8. A tangible, non-transitory, computer-readable medium configured to store instructions executable by a processor of a borescope system, wherein the instructions comprise instructions to:
instruct, using the processor, a display of the borescope system to display a settings menu, wherein the settings menu is configured to enable selection of an articulation mode setting used to control articulation of a probe of the borescope system; and
instruct, using the processor, the display to automatically display a live menu view when the articulation mode setting is selected by a first user input, wherein the live menu view comprises:
a first image captured by the probe; and
a second image of a soft control overlaid on the first image to enable adjustment of an articulation sensitivity setting of the probe via a second user input and control over articulation of the probe via a third user input based at least in part on the articulation mode setting and the articulation sensitivity setting while images captured by the probe are displayed on the display, wherein the articulation sensitivity setting indicates an amount the probe moves in response to the third user input.

9. The computer readable medium of claim 8, wherein the instruction to automatically display the live menu view comprise instructions to instruct, using the processor, an input device of the borescope system to detect the second user input, wherein the second user input increase or decreases the articulation sensitivity setting of the probe.

10. The computer readable medium of claim 9, wherein:
the soft control comprises a first soft button configured to increase the articulation sensitivity setting when activated by the second user input; and
the live menu view comprises a third image of a second soft button overlaid on the first image, wherein the second soft button is configured to decrease the articulation sensitivity setting when activated by the second user input.

11. The computer readable medium of claim 9, wherein the first soft control comprises a slider configured to increase the articulation sensitivity setting when the second user input slides the slider right and to decrease the articulation sensitivity setting when the second user input slides the slider left.

12. The computer readable medium of claim 8, comprising instructions to instruct, using the processor, the borescope system to exit the Live menu view and return to the settings menu after a fourth user input indicates completion of adjustments to the articulation sensitivity setting of the probe.

13. The computer readable medium of claim 12, wherein the live menu view comprises a third image of a soft button overlaid on the first image, wherein the soft button is configured to detect the completion of the adjustments to the articulation sensitivity setting when selected by the fourth user input.

14. A method of controlling articulation of a probe in a borescope system, comprising:
displaying, using a display of the borescope system, a settings menu comprising an articulation mode setting of the probe;
detecting, using input devices of the borescope system, a first user input selecting the articulation mode setting;
displaying, using the display, a live menu view when the first user input is detected, wherein the live menu view comprises:
a first image captured by the probe; and
a second image of a soft control overlaid on the first image to enable a second user input to adjust an articulation sensitivity setting of the-probe via the soft control and to enable a third user input to control articulation of the probe based at least in part on the articulation sensitivity setting while the images captured by the probe are displayed, wherein the articulation sensitivity setting indicates an amount the probe moves in response to the third user input.

15. The method of claim 14, wherein enabling the second user input to adjust the articulation sensitivity setting comprises:
detecting, using the user input devices, the second user input; and
increasing or decreasing, using the borescope system, the articulation sensitivity setting of the probe based at least in part on the second user input.

16. The method of claim 15, wherein:
the first soft control comprises a first soft button configured to increase the articulation sensitivity setting when activated by the second user input; and
the live menu view comprises a third image of a second soft button configured to decrease the articulation sensitivity setting when activated by the second user input.

17. The method of claim 15, wherein the soft control comprises a slider configured to increase the articulation sensitivity setting when the second user input slides the slider right and to decrease the articulation sensitivity setting when the second user input slides the slider left.

18. The method of claim 14, comprising:
detecting, using the input devices, a third user input indicating desire to adjust the articulation sensitivity setting; and displaying, using the display, the live menu view when the third user input is detected.

19. The method of claim 14, wherein the live menu view comprises a third image of a soft button overlaid on the first image, wherein the soft button is configured to indicate completion of adjustment of the articulation sensitivity setting when selected by a third user input.

20. The method of claim 14, wherein detecting the first user input comprises determining whether the first user input selects a proportional mode or a steer & stay mode.

* * * * *